United States Patent [19]

Lakin et al.

[11] Patent Number: 5,300,301
[45] Date of Patent: Apr. 5, 1994

[54] ISOLATION OF IBUPROFEN FROM TABLETS

[75] Inventors: Michael B. Lakin; Thomas H. Shockley; Edward G. Zey, all of Corpus Christi, Tex.

[73] Assignee: Hoechst Celanese Corporation, Somerville, N.J.

[21] Appl. No.: 984,606

[22] Filed: Dec. 2, 1992

[51] Int. Cl.⁵ .......................... A61K 9/14; A61K 9/20
[52] U.S. Cl. ................................... 424/464; 424/484; 424/489; 514/557
[58] Field of Search ................ 424/464, 465, 489

[56] References Cited

U.S. PATENT DOCUMENTS

| | | | |
|---|---|---|---|
| 4,476,248 | 10/1984 | Gordon et al. | 562/494 |
| 5,151,551 | 9/1992 | Zey et al. | 562/494 |
| 5,189,208 | 2/1993 | Stahly | 562/460 |

*Primary Examiner*—Thurman K. Page
*Assistant Examiner*—James M. Spear
*Attorney, Agent, or Firm*—James J. Mullen; Donald R. Cassady; Joseph M. Mazzarese

[57] ABSTRACT

Ibuprofen is isolated from tablets or other solids by dissolving the ibuprofen in an alkane or cycloalkane solvent, filtering off undissolved solid, and stripping the solvent from the ibuprofen by evaporation or by recrystallization at low temperatures.

8 Claims, No Drawings

ISOLATION OF IBUPROFEN FROM TABLETS

BACKGROUND OF THE INVENTION

This invention relates to a process for the isolation of ibuprofen from solids, and especially to a solvent extraction process for isolating ibuprofen from tablets.

Ibuprofen (2-[4'-isobutylphenyl]propionic acid) is a widely used analgesic, and is contained in a variety of over-the-counter medications. These are generally sold in tablet form; these tablets may have a variety of shapes and may be coated, e.g., sugar-coated, polymer film-coated, or the like. These tablets typically contain excipients, lubricants, binders, disintegrants, and/or fillers. The tablet compositions vary depending on the desired dosage, the tablet size, the chosen manufacturing method, and other factors. Examples of ibuprofen-containing tablets, well-known and commercially available in pharmacies throughout the United States and elsewhere, include ADVIL®, COADVIL®, MOTRIN® IB, and NUPRIN®.

ADVIL® is a sugar-coated tablet comprising 200 mg ibuprofen, acacia, acetylated monoglycerides, carnauba wax or beeswax, calcium sulfate, colloidal silicon dioxide, dimethicone, iron oxide, lecithin, pharmaceutical glaze, povidone, sodium benzoate, sodium carboxymethylcellulose, starch, stearic acid, sucrose, and titanium dioxide.

COADVIL® is a sugar-coated tablet comprising 200 mg ibuprofen, 30 mg pseudoephedrine HCl, carnauba wax or equivalent wax, croscarmellose sodium, iron oxides, methylparaben, microcrystalline cellulose, propylparaben, silicon dioxide, sodium benzoate, sodium lauryl sulfate, starch, stearic acid, sucrose, and titanium dioxide.

MOTRIN® IB is a film-coated tablet comprising 200 mg ibuprofen, carnauba wax, cornstarch, hydroxypropyl methylcellulose, propylene glycol, silicon dioxide, pregelatinized starch, stearic acid, and titanium dioxide.

NUPRIN® is a film-coated tablet comprising 200 mg ibuprofen, carnauba wax, cornstarch, D&C Yellow No. 10, FD&C Yellow No. 6, hydroxypropyl methylcellulose, silicon dioxide, stearic acid, and titanium dioxide.

In the manufacture of such tablets, it is expected that a certain percentage of tablets will not meet all the manufacturing specifications, and cannot be sold or used. Unless the ibuprofen can be recycled, the ibuprofen in these off-spec tablets will be wasted, raising manufacturing and consumer costs and wasting natural resources. However, recycling is not economically feasible unless it can be done cheaply and produce ibuprofen pure enough to meet drug quality standards.

The recycling or recovery of ibuprofen from tablets is complicated by the presence of other ingredients, e.g. fillers and excipients, and by the use of tablet coatings. The ibuprofen must be well-separated from these substances to obtain the requisite drug purity. At the same time, it is desirable to obtain an ibuprofen yield that is as high as possible. If a film or other tablet coating is removed in a preisolation process, e.g., by physical abrasion, this additional step may increase costs and cause loss of tablet material, reducing yield.

A method for recovering ibuprofen and its salts by recrystallization and catalytic dehalogenation of the filtrate is disclosed in the *Chemical Abstract* 108:5688p of Japanese patent 62-185, 041 (1987) In this process, a crude solution in hexane is cooled to precipitate ibuprofen, and the filtrate is evaporated to obtain a chloride salt which is dissolved in 2% NAOH and heated over Pd catalysts to obtain ibuprofen.

A method for purifying ibuprofen is disclosed in the *Chemical Abstract* 109:73144d of Japanese patent 62-294,637 (1987). In this method, a mixture of crude ibuprofen and molecular sieves in hexane is refluxed, cooled, filtered, and cooled to 0° C. to produce pure ibuprofen.

A method for determining ibuprofen in plasma by reversed-phase HPLC is disclosed in the *Chemical Abstract* 112:111406n of Chinese reference *Sepu*, 7(6), 357-8 (1989). In this method, ibuprofen is extracted from acidified plasma using a hexane-isopropanol (9:1) solvent and detected by HPLC.

A method for determining ibuprofen and its metabolites in human urine by HPLC is disclosed in Chai, et al., "Determination Of Ibuprofen And Its Major Metabolites In Human Urine By High-Performance Liquid Chromatography", *J. Chromatography*, 430, 93–101 (1988). In this process, urine is acidified, extracted into hexane-propanol, and back-extracted into sodium bicarbonate, then neutralized and chromatographed. The extraction efficiencies were reported to be 94–100% for all compounds.

SUMMARY OF THE INVENTION

The present invention is a process for isolating ibuprofen from an ibuprofen-containing solid comprising: combining said solid with a solvent chosen from alkanes and cycloalkanes having 5–7 carbon atoms at a temperature of at least about 35° C. to dissolve said ibuprofen in said solvent and form an ibuprofen-containing solution; filtering said solution to remove undissolved solid; and, separating said ibuprofen from said solvent, wherein said separation step may comprise either evaporating said solvent or cooling said solution to cause said ibuprofen to crystallize from said solution.

Preferably, the solid is ground or crushed in a preprocessing step; this is important to facilitate the isolation process where the solid exists as one or more large pieces, e.g., as a tablet, but is not necessary where the solid is in the form of small particles, such as powder or granules.

It is an object of the present invention to provide a process for isolating ibuprofen from other ingredients contained in an ibuprofen-containing tablet.

It is a further object of the present invention to provide an extraction process for isolating ibuprofen from solids partially made of ibuprofen.

It is another object of the present invention to provide a process for economically recovering and purifying ibuprofen contained in tablets and powders.

Other objects and advantages of the present invention will be apparent to those skilled in the art from the following description and from the appended claims.

DETAILED DESCRIPTION OF THE PREFERRED EMBODIMENTS

In one preferred embodiment of the present invention, a quantity of sugar-coated tablets containing ibuprofen (about 40–60% by weight) and excipients, lubricants, binders, disintegrants, and/or fillers (e.g., ADVIL® tablets, or the like) is ground into a powder and combined with hexane in an amount about twice the mass of the tablets. The mixture is heated to boiling or near boiling and stirred well for about 10–60 minutes to dissolve the ibuprofen. The mixture is then filtered to separate the ibuprofen solution from the undissolved solids (excipients, sugar coating, etc.).

Ibuprofen crystals are recovered from the solution by solvent stripping. In one preferred solvent removal method, the solution is cooled to a temperature of about 5°–10° C. or less, causing the ibuprofen to precipitate. Alternatively, the solvent may be evaporated from the solution, leaving solid ibuprofen behind. In both cases, the purity of the recovered ibuprofen is high, generally about 99.7% or higher. For crystallization, the yield is at least about 95% of the total ibuprofen in the tablets; the evaporation procedure can produce even greater yields, such as 98% or more.

If desired, the yield may be increased somewhat by washing the filtered undissolved solids with hexane and solvent stripping the wash liquid, either separately or together with the solution. The yield may also be increased in the recrystallization procedure, where a small percentage of the ibuprofen can be expected to remain in solution at the recrystallization temperature, by a second recovery step in which solvent is stripped from the crystallization mother liquor to concentrate this solution so that additional ibuprofen crystallization may occur.

Those skilled in the art will appreciate the large variety of evaporation procedures that are available for solvent stripping. One example of a suitable procedure is to use a rotoevaporator in which the temperature is maintained at about 50° C. and the atmospheric pressure is reduced to 20–25 inches Hg by applying a partial vacuum. The evaporation rate will increase with increasing temperature and decreasing pressure. Any effective evaporation method that does not lead to significant loss of ibuprofen is suitable in the practice of this invention.

If the invention is practiced on an ibuprofen-containing powder, a grinding step in unnecessary. Where a solid mass (e.g., a typical tablet) must be extracted it is important to reduce the mass r-o small particles or powder to facilitate dissolution of the ibuprofen. Any conventional grinding or crushing method may be used, including, but not limited to, manually grinding the mass with a mortar and pestle, crushing the mass with a heavy weight, putting the mass in an electric blender, grinding the mass a mill, and so forth.

The solvent may be any liquid that dissolves ibuprofen but not the other ingredients of the solid being extracted, provided that the solvent may be separated from the ibuprofen afterward without destroying the ibuprofen. In a commercial setting, the cost and availability of the solvent is also important. Preferred solvents in the practice of this invention include heptane, hexane, pentane, cyclohexane and combinations thereof. Whether the solvent is stripped using cooling/recrystallizing or using evaporation, those skilled in the art will appreciate that the process may be set up to allow recycling of the stripped solvent to reduce costs and avoid wasting resources.

Although the solvent may be boiled to facilitate dissolving the ibuprofen, boiling is not required. However, the solution should be heated to at least about 35° C. to dissolve essentially all the ibuprofen. The amount of heating and stirring time needed to completely dissolve the ibuprofen will vary as a function of the temperature, the solvent, the ibuprofen content of the solid, the amount of solid, and the ratio of solvent to solid. Generally, 10–60 minutes of heating, with vigorous stirring, is sufficient. Those skilled in the art will be able to determine the appropriate amount of time in a given instance without undue experimentation.

Alternative ibuprofen extraction techniques known in the art may be used to dissolve the ibuprofen in the solvent, such as Soxhlet extraction, and the like; of course, the amount of ibuprofen recovered may be reduced if a less effective technique is chosen.

The percentage of ibuprofen in the solid is not critical in the practice of the invention, although it is understood that the optimum proportion of solvent to solid may vary with varying ibuprofen content. This proportion may also vary as a function of the solvent chosen and the specific procedural parameters used (i.e., temperature, solvent stripping method, etc.). The ratio of solvent to solid should be chosen to produce a workable slurry.

The procedure described above for recovering ibuprofen from sugar-coated tablets may also be used to recover ibuprofen from film-coated tablets containing ibuprofen (e.g., MOTRIN ® IB, and NUPRIN ®) This procedure may also be used with ibuprofen-containing powders, except that the pre-extraction grinding step would be eliminated.

The following Examples are presented to further illustrate the present invention. However, the invention should not be construed as limited to the illustrated embodiments.

EXAMPLE I

A 110-gram quantity of ADVIL ® sugar-coated ibuprofen tablets were crushed to powder using a mortar and pestle. To this powder was added 220 grams of hexane. The hexane was heated and brought to a boil for 10 minutes, during which time the powder was stirred into the hexane solvent to dissolve ibuprofen.

The mixture was filtered through a coarse fritted glass funnel to remove undissolved solids, i.e., excipient and coating, from the ibuprofen-containing hexane solution. The hexane was then evaporated from the solution at a temperature of 50° C. and a pressure of 20–25 inches Hg (508°–635 torr), leaving ibuprofen crystals.

This same procedure was used on MOTRIN ® and COADVIL ® tablets.

The amount and purity of the ibuprofen recovered in each case was measured using standard U.S. Pharmacopeia and British Pharmacopeia procedures. Table I presents the results of these three experiments. The material recovered in each case was of suitable quality to be purified to USP grade ibuprofen by conventional methods.

TABLE I

| | % IBU Recovered | Assay* % IBU | % IBU by HPLC | % Org. Imp. by HPLC |
|---|---|---|---|---|
| ADVIL | 96.4 | 100.1 | 99.9 | 0.13 |
| MOTRIN | 99.8 | 99.4 | 100.1 | 0.29 |
| COADVIL | 98.1 | 97.9 | 96.6 | 0.18 |

*By direct titration.
IBU = ibuprofen;
HPLC = high performance liquid chromatography;
Org. Imp. = organic impurities.

EXAMPLE II

Ibuprofen was recovered from ADVIL ® and MOTRIN ® tablets using the same procedure as in Example I, except that instead of evaporating solvent the ibuprofen was separated from the solvent by cooling the solution to 5° C. and maintaining that temperature until recrystallization was complete, and then filtering. The crystals were dried in a vacuum oven at about 508 torr and 45° C. Table II presents the results of these two experiments; measurements were done according to the procedures used in Ex. I.

TABLE II

|        | Assay* % IBU | % IBU by HPLC | % Org. Imp. by HPLC |
|--------|--------------|---------------|---------------------|
| ADVIL  | 99.0         | 96.7          | 0.05                |
| MOTRIN | 99.9         | 96.0          | 0.13                |

*By direct titration.
IBU = ibuprofen;
HPLC = high performance liquid chromatography;
Org. Imp. = organic impurities.

Many variations and equivalents of the present invention will occur to those skilled in the art. The present invention is not limited to the embodiments illustrated or described, but includes all the subject matter within the spirit and scope of the appended claims and of the foregoing disclosure.

We claim:

1. A process for isolating ibuprofen from an ibuprofen-containing solid, said solid containing an excipient, filler, binder, lubricant or disintegrant, said process comprising:
    combining said solid with a solvent chosen from alkanes and cycloalkanes having 5-7 carbon atoms at a temperature of at least about 35° C. to dissolve said ibuprofen in said solvent and form an ibuprofen-containing solution;
    filtering said solution to remove undissolved solid; and,
    separating said ibuprofen from said solvent, wherein said process isolates at least about 95% of the ibuprofen contained in said solid.

2. A process as set forth in claim 1 wherein said separation step comprises cooling said solution to a temperature at which said ibuprofen will recrystallize from said solution.

3. A process as set forth in claim 1 wherein said separation step comprises evaporating said solvent from said solution.

4. A process as set forth in claim 1 further comprising crushing or grinding said solid to a powder prior to said combining step.

5. A process as set forth in claim 1 wherein said solvent is chosen from the group consisting of pentane, hexane, heptane, and cyclohexane.

6. A process for isolating ibuprofen from an ibuprofen-containing solid, said solid containing an excipient, filler, binder, lubricant or disintegrant, said process comprising:
    crushing or grinding said solid to a powder;
    combining said solid with a solvent chosen from the group consisting of pentane, hexane, heptane, and cyclohexane at a temperature of at least about 35° C. to dissolve said ibuprofen in said solvent and form an ibuprofen-containing solution;
    filtering said solution to remove undissolved solid; and,
    separating said ibuprofen from said solvent, wherein said process isolates at least about 95% of the ibuprofen contained in said solid.

7. A process as set forth in claim 6 wherein said separation step comprises cooling said solution to a temperature at which said ibuprofen will recrystallize from said solution.

8. A process as set forth in claim 6 wherein said separation step comprises evaporating said solvent from said solution.

* * * * *

UNITED STATES PATENT AND TRADEMARK OFFICE
CERTIFICATE OF CORRECTION

PATENT NO. : 5,300,301
DATED : April 5, 1994
INVENTOR(S) : Michael B. Lakin, Thomas D. Shockley; Edward G. Zey It is certified that error appears in the above-indentified patent and that said Letters Patent is hereby corrected as shown below:

Column 6, line 21, insert "powder" after --solid --.

Signed and Sealed this

Twenty-sixth Day of July, 1994

Attest:

BRUCE LEHMAN

Attesting Officer                Commissioner of Patents and Trademarks